United States Patent
Chrysopoulo et al.

(10) Patent No.: US 8,399,002 B2
(45) Date of Patent: Mar. 19, 2013

(54) TOPICAL SCAR TREATMENT COMPOSITION

(75) Inventors: Minas Chrysopoulo, San Antonio, TX (US); Roland Hoffman, San Antonio, TX (US); Susan Goldsberry, Huntington Beach, CA (US)

(73) Assignee: C & H Scientific, LLC, San Antonio, TX (US)

( * ) Notice: Subject to any disclaimer, the term of this patent is extended or adjusted under 35 U.S.C. 154(b) by 0 days.

(21) Appl. No.: 12/987,115

(22) Filed: Jan. 8, 2011

(65) Prior Publication Data

US 2011/0171156 A1    Jul. 14, 2011

Related U.S. Application Data

(60) Provisional application No. 61/293,456, filed on Jan. 8, 2010.

(51) Int. Cl.
*A61K 8/02* (2006.01)
(52) U.S. Cl. .................... 424/401; 424/78.08
(58) Field of Classification Search .................. None
See application file for complete search history.

(56) References Cited

U.S. PATENT DOCUMENTS

2002/0028844 A1* 3/2002 Fitzpatrick et al. ........... 514/474

OTHER PUBLICATIONS

Chrysopoulo, Scar Treatment Facts, Which scar treatments are backed by Science?, available online Oct. 20, 2009.*
Letawe et al. Digital Image analysis of the effects of topically applied linoleic acid on acne microcomedones, Clinical and Experimental Dermatology, vol. 23, Issue 2, pp. 56-58, Mar. 1998.*
Ale vera from Vitality Unlimited, published online 1989.*
Zenmed, How Our Rosacea System Works, Available online Feb. 22, 2003.*

* cited by examiner

*Primary Examiner* — Anand Desai
*Assistant Examiner* — Melissa Mercier
(74) *Attorney, Agent, or Firm* — Louis C. Paul

(57) ABSTRACT

An anhydrous topical scar treatment product having a water activity of less than 0.50, the product being comprised of (i) a silicone elastomer, (ii) a non-volatile, anhydrous carrier vehicle, (iii) L-ascorbic acid in the form of fine powder, at a concentration of concentration of from 7.5% to 15% by weight, based on the total weight of the anhydrous topical scar treatment product, and (iv) an oil-soluble Vitamin C derivative at a concentration of from 5% to 10% by weight, based on the total weight of the anhydrous topical scar treatment product.

16 Claims, No Drawings

TOPICAL SCAR TREATMENT COMPOSITION

CROSS REFERENCE TO RELATED APPLICATION

This application claims priority to U.S. Provisional Application Ser. No. 61/293,456 filed on Jan. 8, 2010, the disclosure of which is incorporated herein by reference in its entirety.

FIELD OF INVENTION

The present invention is directed to an anhydrous topical formulation used for preventing and/or reducing the appearance of scars and stretch marks.

BACKGROUND OF THE INVENTION

The use of silicones—fluids, elastomers and resins—in topical products is well-known in the art. See, e.g, Starch, *New Developments in Silicone Elastomers for Skin Care* (Dow Corning Corp., 2002).

US Patent Application Publication No. 2009/0143333 describes a topical wound healing composition comprising a cyclic siloxane, a silicone occlusive fluid, a silicone occlusive gel, and a silicone resin powder.

The use of topical silicone in the treatment of scarring has been described in the prior art. See, e.g, Chernoff, et al., *Aesthetic Plast Surg.* Vol. 31, No. 5, pp. 495-500 (September-October 2007) (use of topical silicone gel elastomers in the treatment of hypertrophic scars, keloid scars, and post-laser exfoliation erythema); Gold et al., *Dermatol Surg.* Vol. 27, No. 7, pp. 641-4 (July 2001) (use of topical silicone gel sheets post surgery to prevent hypertrophic and keloid scars); Clugston et al., *Ann. Plast Surg.* Vol. 34, No. 1, pg. 12-5 (January 1995) (use of topical silicone gel sheets to promote early wound healing after linear incisions).

U.S. Pat. No. 6,027,738 claims anhydrous makeup composition for topical application to the skin comprising (i) a silicone gel, the gel comprising an organopolysiloxane elastomer dispersed in a silicone-compatible vehicle, (ii) and a silicone-oil base.

European Patent Application EP1707189A2 teaches the use of oleo-distillates, unsaponifiables and/or furan lipids from sunflower seed oil in cosmetic or dermatological composition for promoting the synthesis of cutaneous lipids.

Peroxisome-proliferator-activated receptor-alpha (PPAR) receptors modulate the expression of various genes, which interfere with the metabolism and transport of lipids. According to trade literature from Barnet Products Corporation (Englewood Cliffs, N.J.), a mixture of unsaponifiables from *Helianthus Annuus* (Sunflower) Seed Oil obtained by molecular distillation and offered for sale under the tradename Soline is PPAR-alpha agonist.

In addition to its known skin moisturizing properties (i.e., emolliency), aloe vera has also been described as having anti-inflammatory, antibacterial and antifungal properties. The precise constituents of aloe vera responsible for these physiological activities remain to be elucidated. See, *Crit. Rev. Food. Sci. Nutr.* Vol. 44, No 2, pp. 91-6 (2004).

SUMMARY OF THE INVENTION

The present invention is directed to an anhydrous topical scar treatment product comprising a silicone elastomer and non-volatile, anhydrous carrier vehicle, most preferably a low-viscosity dimethylpolysiloxane, and a scar-minimizing complex consisting essentially of aloe vera, a licorice extract ester, at least one essential fatty acid (EFA), and an omega-9 fatty acid.

DETAILED DESCRIPTION OF THE INVENTION

As used in the present application, an anhydrous product is one having water activity ($a_w$) of less than about 0.5, where water activity is defined by the equation $a_w = p/p_o$. and "p" and "$p_o$" are, respectively, the partial pressures of water in the product and in a solution of pure water under identical conditions of pressure and temperature.

The silicone elastomer used in the topical scar treatment product of the present invention is preferably a silicone elastomer in a non-volatile, low viscosity dimethicone. By silicone elastomer is meant cross-linked linear silicone polymers.

Dimethicone Crosspolymer is a polymer formed by crosslinking dimethicone with a $C_3$-$C_{20}$alkyl group. More particularly, a dimethyl/methylhydrogen polymer is reacted by a solvent process with an organic group having an alpha diene and/or alpha,omega diene. In a "suspension" process, the dimethyl/methylhydrogen copolymer is dissolved in a solvent selected from the group consisting of cyclomethicone, low-viscosity dimethicones and hydrocarbons, including isododecane.

A "solvent" process may also be used to form silicone elastomers suitable for use in the scar treatment product of the present invention. More particularly, an aqueous suspension is created from dimethyl/methylhydrogen copolymer and a silanol-terminated or ethenyl-terminated polydimethylsiloxane, commonly abbreviated in the art as PDMS.

PDMS is an organosilicon polymer having a backbone of alternating Si—O—Si units. (Two methyl groups are present on each silicon atom.) PDMS is formed by reacting a silicon metal with methyl chloride, producing methyl chlorosilanes. Methyl chlorosilanes are distilled to dimethyldichlorosilane conforming to the formula $(CH_3)_2SiCl_2$.

In a preferred embodiment the silicone elastomer is a blend of the elastomer in a non-volatile, low viscosity dimethicone fluid—Dimethicone Crosspolymer in 5 centistoke dimethicone available from Dow Corning under the tradename Dow Corning 9041 (INCI: Dimethicone (and) Dimethicone Crosspolymer). Technical literature from Dow Corning teaches that this silicone elastomer blend can be used as a binder in pressed powder cosmetics.

Other silicone elastomers suitable for use in the present invention are Dimethicone Crosspolymer-3 and Polysilicone-11.

Dimethicone Crosspolymer-3 conforms to the structure:

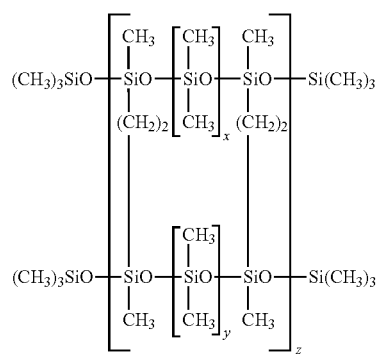

Polysilicone-11 is a crosslinked siloxane formed by the reaction of a ethenyl-terminated siloxane and methylhydroxydimethyl siloxane in the presence of cyclomethicone.

Preferably, the silicone elastomer blend (silicone elastomer in low-viscosity dimethicone) is present at a concentration of from about 60% to about 75% by weight, based on the total weight of the topical scar treatment product, more preferably from about 65% to about 70% by weight.

The silicone elastomer blend is preferably further combined with a non-volatile anhydrous carrier vehicle, most preferably a low-viscosity dimethylpolysiloxane.

Preferably, the low-viscosity dimethylpolysiloxane has a viscosity ranging from 1 to 50 centistokes, more preferably having a viscosity of less than 25 centistokes, still more preferably having a viscosity of less than 10 centistokes. A non-limiting example of a particularly preferred low-viscosity dimethylpolysiloxane is Dimethisil DM-6 having viscosity of 6 centipoise and a specific gravity of 0.925 (approx. 6.5 centistoke).

Preferably, the non-volatile anhydrous carrier vehicle, is present at a concentration of from about 10% to about 20% by weight, based on the total weight of the topical scar treatment product, more preferably from about 10% to about 15% by weight.

In a particularly preferred embodiment, the silicone elastomer blend and the non-volatile anhydrous carrier vehicle are present at a combined concentration of at least 80% by weight, based on the total weight of the topical scar treatment product.

Vitamin C is a multifunctional ingredient that is widely-used in topical formulations. Among its many desirable therapeutic properties are an ability to quench free radicals (antioxidant), to lighten dark/pigmented areas of the skin (inhibition of intracellular tyrosinase and melanogenesis), to promote collagen synthesis, and to reduce UV-induced cell damage, including by inhibiting lipid peroxidation.

The scar treatment product of the present invention comprises two forms of Vitamin C: (i) water-soluble fine powder of L-ascorbic acid and (ii) an oil soluble Vitamin C derivative.

The fine powder of L-ascorbic acid is a white to slightly yellow powder. It is a chiral molecule, having an empirical formula of $C_6H_8O_6$ and conforming to the structure:

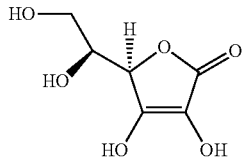

As used in the present application, by fine powder is meant a powder having the following particle sizes (i.e., fineness) as measured by a US Sieve Series: at least 99% pass through a No. 100 Series US Sieve and at least 90% pass through a No. 200 Series US Sieve. Fine powder of L-ascorbic acid meeting these criteria are available from DSM Nutritional Products, Inc. (Parsippany, N.J.).

In a preferred embodiment, the fine powder of L-ascorbic acid is present in the topical scar treatment product at a concentration of from about 7.5% to about 15% by weight, preferably from about 10% to about 15% by weight, based on the total weight of the topical scar treatment product.

It is known in the art that Vitamin C derivatives can be unstable and, consequently, lose their potency. Additionally, many Vitamin C derivatives are not readily absorbed in the skin. Accordingly, the scar treatment product of the present invention comprises an oil-soluble Vitamin C derivative. The latter property allows for more efficacious percutaneous absorption and, consequently, a higher rate of conversion of the Vitamin C derivative into free Vitamin C.

In a preferred embodiment, the oil-soluble Vitamin C derivative is tetrahexyldecyl ascorbate conforming to the structure:

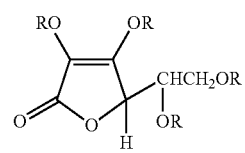

This Vitamin C derivative is commercially available under the tradename BV-OSC from Barnet Products Corp.

In a preferred embodiment, the oil-soluble Vitamin C derivative, preferably, is present in the topical scar treatment product at a concentration of from about 5% to about 10% by weight, preferably from about 7% to about 10% by weight, based on the total weight of the topical scar treatment product.

In a particularly preferred embodiment, the fine powder of L-ascorbic acid and oil-soluble Vitamin C derivative, preferably tetrahexyldecyl ascorbate, are present at a combined concentration of from about 15% to about 20% by weight, based on the total weight of the topical scar treatment product.

In addition to the fine Vitamin C powder and oil-soluble Vitamin C derivative, the scar treatment product of the present invention contains a scar-minimizing complex consisting of aloe vera, a licorice extract ester, and at least one essential fatty acid (EFA) and an omega-9 fatty acid.

Licorice extract esters suitable for use in the scar-minimizing complex include saturated and unsaturated esters of glycerrhetic acid and glycyrrhizic acid in which the ester portion of the molecule contains from 2 to 24 carbon atoms, more preferably from 10 to 24 carbon atoms, still more preferably from 16 to 24 carbon atoms. Representative, non-limiting licorice extract ester derivatives include but are not limited to monoammonium glycyrrhizinate, monopotassium glycyrrhizinate, dipotassium glycyrrhetinic acid, disodium 3-succinyloxy-beta-glycyrrhetinate, and the like.

Stearyl glycyrrhetinate, available under the tradename NET-STG from Barnet Products Corp. is a preferred licorice extract ester, and is preferably present at a concentration of from about 0.01% to about 1.0% by weight, based on the total weight of the topical scar treatment product. More preferably, the licorice extract ester is present at a concentration of at from about 0.1% to about 1.0% by weight, based on the total weight of the topical scar treatment product Aloe vera is an article of commerce available from a number of raw material suppliers, including Active Organics LLC (Lewisville, Tex.) under the tradename Actiphyte of Aloe Vera Lipo S. Preferably, aloe vera is present at a concentration of at from about 0.1% to about 1.0% by weight, based on the total weight of the topical scar treatment product.

Preferably, the licorice extract ester is present in a ratio of about 1:1 to aloe vera.

As used in the present application, by the term "essential fatty acid" is meant an 18-carbon carboxylic acid having two or three cis double bonds. EFAs suitable for use in the scar-minimizing complex of the present invention are selected from the group of linoleic acid (IUPAC cis, cis-9,12-octadecadienoic acid), a polyunsaturated ω-6 fatty acid with two cis double bonds and α-linolenic acid (IUPAC 9,12,15-octadecatrienoic acid), a polyunsaturated ω-3 fatty acid with three cis double bonds.

Preferably, the EFA is linoleic acid. Preferably, linoleic acid is present at a concentration of from about 0.1% to about 1.0%, by weight of the scar treatment product. More preferably, linoleic acid is present at a concentration of from about 0.2% to about 0.8%, by weight of the scar treatment product. Still more preferably, linoleic acid is present at a concentration of from about 0.4% to about 0.6%, by weight of the scar treatment product.

Sources of linoleic acid include, but are not limited to, *Euterpe oleracea* (Acai) Fruit Oil, *Borago Officinalis* (Borage) Seed Oil, *Ribes Nigrum* (Blackcurrant) Seed Oil, *Gossypium Barbadense* (Cotton) Seed Oil, *Zea Mays* (Corn) Oil, *Oenothera Biennis* (Evening Primrose) Oil, *Linum Usitatissimum* (Linseed) Seed Oil, *Cucurbita Pepo* (Pumpkin) Seed Oil, *Cannabis Sativa* (Hemp) Seed Oil, *Carthamus Tinctorius* (Safflower) Seed Oil, *Glycine Soja* (Soybean) Oil, *Helianthus Annuus* (Sunflower) Seed Oil. Preferably, the source of linoleic acid in the scar-minimizing complex is *Helianthus Annuus* (Sunflower) Seed Oil.

In a particularly preferred embodiment, the ratio of the combined amounts of licorice extract ester and aloe vera to the at least one essential fatty acid is about 1:3.

Oleic acid is a mono-unsaturated omega-9 fatty acid having the molecular formula $C_{18}H_{34}O_2$. Preferably, oleic acid is present at a concentration of from about 0.05% to about 0.5%, by weight of the scar treatment product. More preferably, oleic acid is present at a concentration of from about 0.1% to about 0.3%, by weight of the scar treatment product.

Sources of oleic acid include, but are not limited to, *Olea Europaea* (Olive) Fruit Oil, *Helianthus Annuus* (Sunflower) Seed Oil, *Elaeis Guineensis* (Palm) Kernel Oil, and *Arachis Hypogaea* (Peanut) Oil. Preferably, the source of oleic acid in the scar-minimizing complex is *Helianthus Annuus* (Sunflower) Seed Oil.

In another particularly preferred embodiment, the ratio of the combined amounts of licorice extract ester and aloe vera to oleic acid is about 1:1.

The following formulation example is illustrative of the present invention. The components and specific ingredients are presented as being typical, and various modifications can be derived in view of the foregoing disclosure within the scope of the invention.

| | |
|---|---|
| Dimethicone (and) Dimethicone Crosspolymer | 65.00-70.00 |
| Low-viscosity dimethylpolysiloxane | 10.00-15.00 |
| Ascorbic Acid (Fine Powder) | 10.00-15.00 |
| Tetrahexyldecyl ascorbate | 5.00-10.00 |
| *Helianthus annuus* (Sunflower) Seed Oil | 0.50-2.00 |
| *Aloe vera* | 0.1-0.5 |
| Stearyl glycyrrhetinate | 0.1-0.5 |

Into the main vessel, add dimethicone (and) dimethicone crosspolymer. In a first side vessel, mix low-viscosity dimethylpolysiloxane, ascorbic acid (fine powder) and tetrahexyldecyl ascorbate. Add contents of first side vessel to main vessel; mix until uniform. In a second side vessel, prepare scar-minimizing complex by mixing *Helianthus annuus* (sunflower) seed oil, Aloe vera and stearyl glycyrrhetinate. Add scar-minimizing complex to main vessel. Mix until uniform.

All documents cited herein are, in relevant part, incorporated herein by reference; the citation of a document is not, however, to be construed as an admission that it is prior art with respect to the present invention. To the extent that there is a conflict between the use of a term in this application and a document incorporated by reference, the meaning or definition in this application should be applied. While particular embodiments of the present invention have been illustrated and described, changes and modifications can be made without departing from the spirit and scope of the invention.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. An anhydrous topical scar treatment product comprising (i) a silicone elastomer, (ii) a non-volatile, anhydrous carrier vehicle, (iii) L-ascorbic acid in the form of fine powder, said fine powder being present at a concentration of concentration of from 7.5% to 15% by weight, based on the total weight of the anhydrous topical scar treatment product, (iv) an oil-soluble Vitamin C derivative at a concentration of from 5% to 10% by weight, based on the total weight of the anhydrous topical scar treatment product, and (v) a scar-minimizing complex consisting of (a) aloe vera, (b) a licorice extract ester, (c) at least one essential fatty acid, and (d) an omega-9 fatty acid, wherein the anhydrous topical scar treatment product has a water activity of less than 0.50.

2. An anhydrous topical scar treatment product comprising (i) a silicone elastomer, (ii) low viscosity dimethylpolysiloxane having a viscosity of less than 50 centistokes as a non-volatile, anhydrous carrier vehicle (iii) L-ascorbic acid in the form of fine powder, said fine powder being present at a concentration of concentration of from 7.5% to 15% by weight, based on the total weight of the anhydrous topical scar treatment product, (iv) an oil-soluble Vitamin C derivative at a concentration of from 5% to 10% by weight, based on the total weight of the anhydrous topical scar treatment product, and (v) a scar-minimizing complex consisting essentially of (a) aloe vera, (b) a licorice extract ester, (c) at least one essential fatty acid, and (d) an omega-9 fatty acid, wherein the anhydrous topical scar treatment product has a water activity of less than 0.50 and wherein the non-volatile, anhydrous carrier vehicle is a low-viscosity dimethylpolysiloxane having a viscosity of less than 50 centistokes.

3. The anhydrous topical scar treatment product of claim 2 wherein the silicone elastomer is a blend of dimethicone and dimethicone crosspolymer.

4. The anhydrous topical scar treatment product of claim 2 wherein the silicone elastomer blend and the low-viscosity dimethylpolysiloxane are present at a combined concentration of at least about 80% by weight, based on the total weight of the anhydrous topical scar treatment product.

5. The anhydrous topical scar treatment product of claim 1 wherein the oil-soluble Vitamin C derivative is tetrahexyldecyl ascorbate.

6. The anhydrous topical scar treatment product of claim 1 wherein the licorice extract ester is stearyl glycyrrhetinate, the essential fatty acid is linoleic acid, and the omega-9 fatty acid is oleic acid.

7. The anhydrous topical scar treatment product of claim 6 wherein the licorice extract ester is present in a 1:1 ratio, by weight, to aloe vera and the oleic acid is present in a 1:3 ratio, by weight, to linoleic acid.

8. The anhydrous topical scar treatment product of claim 2 wherein the oil-soluble Vitamin C derivative is tetrahexyldecyl ascorbate.

9. The anhydrous topical scar treatment product of claim 2 wherein the licorice extract ester is stearyl glycyrrhetinate, the essential fatty acid is linoleic acid, and the omega-9 fatty acid is oleic acid.

10. The anhydrous topical scar treatment product of claim 9 wherein the licorice extract ester is present in a 1:1 ratio, by weight, to aloe vera and the oleic acid is present in a 1:3 ratio, by weight, to linoleic acid.

11. The anhydrous topical scar treatment product of claim 1 wherein the non-volatile, anhydrous carrier vehicle is a low-viscosity dimethylpolysiloxane having a viscosity of less than 50 centistokes.

12. The anhydrous topical scar treatment product of claim 1 wherein the silicone elastomer is a blend of dimethicone and dimethicone crosspolymer.

13. The anhydrous topical scar treatment product of claim 1 wherein the silicone elastomer blend and the low-viscosity dimethylpolysiloxane are present at a combined concentration of at least about 80% by weight, based on the total weight of the anhydrous topical scar treatment product.

14. A topically-applied scar-minimizing complex consisting of (a) aloe vera, (b) a licorice extract ester, (c) at least one essential fatty acid, and (d) an omega-9 fatty acid.

15. The topically-applied scar-minimizing complex of claim 14 wherein wherein the licorice extract ester is stearyl glycyrrhetinate, the essential fatty acid is linoleic acid, and the omega-9 fatty acid is oleic acid.

16. The topically-applied scar-minimizing complex of claim 15 wherein the licorice extract ester is present in a 1:1 ratio, by weight, to aloe vera and the oleic acid is present in a 1:3 ratio, by weight, to linoleic acid.

* * * * *